United States Patent [19]

Cotrel

[11] Patent Number: 4,641,636
[45] Date of Patent: Feb. 10, 1987

[54] DEVICE FOR SUPPORTING THE RACHIS
[76] Inventor: Yves P. C. A. Cotrel, Villa Kerosen - Taden, 22100 Dinan, France
[21] Appl. No.: 599,558
[22] Filed: Apr. 12, 1984
[30] Foreign Application Priority Data May 4, 1983 [FR] France ................................. 83 07450

[51] Int. Cl.⁴ ............................................. A61B 17/56
[52] U.S. Cl. .................................... 128/69; 128/92 R; 128/92 YM
[58] Field of Search ............... 128/69, 75, 92 R, 92 F, 128/92 YM

[56] References Cited
U.S. PATENT DOCUMENTS

| 4,047,523 | 9/1977 | Hall | 128/69 |
| 4,409,968 | 10/1983 | Drummond | 128/69 |
| 4,422,451 | 12/1983 | Kalamchi | 128/69 |

FOREIGN PATENT DOCUMENTS

| 3032237 | 3/1982 | Fed. Rep. of Germany | 128/69 |
| 2244446 | 4/1975 | France . | |
| 2096465 | 10/1982 | United Kingdom | 128/69 |
| 624615 | 9/1978 | U.S.S.R. | 128/69 |
| 654251 | 3/1979 | U.S.S.R. | 128/69 |

OTHER PUBLICATIONS

"Spine Instrumentation", Zimmer Catalog, p. D67, Feb. 1973.
Surgeons See New Operation for Correcting Spinal Curvature, The Courier-Journal, Sep. 18, 1984.
NKC Hospitals Host Historic Spine Surgery, NKC News.
New Surgery Will Rid Some Adolescents of Back Braces, Today's Health, Nov. 1984.
A Patient's Tale: Once Was Not Enough, Discover, Dec. 1984.
The Latest Wrinkle in Correcting Scoliosis, American Journal of Nursing, Jan. 1985.
Cotrel-Dubousset Instrumentation for Correction Scoliosis Outlined, Surgical Technique, Interviews, Feb. 1985.
A French Doctor Pioneers a Way to Correct Crooked Spines, People Magazine, Apr. 29, 1985.
Scoliosis: A 30-Second Check-up, McCall's Magazine, May 1985.
New Method of Surgical Treatment for Scoliosis, Backtalk, Summer 1985.
Cotrel-Dubousset Instrumentation for Scoliosis, Backtalk, Summer 1985.
Innovative Surgery Has Alpine Girl Walking Tall, The Daily Californian, Sep. 28, 1985.
Spinal Curvature Corrected, The San Diego Union, Monday, Oct. 7, 1985.
Strasbourg: Une Reunion Organisee Par les Laboratories Specia Chirurgie des Scolioses: Apres l'intervention de Harrington celle de Cotrel, Le Uuotidien Du Medecin, Mardi 15, Oct. 1985.
Standing Straignt, Discover, Dec. 1984.
Essais Comparatifs de Tenue a la Fatigue sur des Tiges Chirurgicales soumises au flambage ou a la flexion repetee Rapport, Laboratoire National D'Essais, Jun. 30, 1982.
Report: Breaking-point and Deformation Study Under Loads of Metallic Equipment (to be implanted in spine surgery), Feb. 27, '85.
Universal Instrumentation (CD) for Spinal Surgery, Stuart, 1985.
Universal Instrumentation (CD) for Spinal Surgery, Sofamor (SFM).
5th Annual Kosair Children's Spine Symposium Hands-on Presentations by French Surgeons Yves Cotrel and Jean Dubousset, Dec. 2 & 3, 1985.
Cotrel-Dubousset Instrumentation for Correction of Scoliosis Outlined Surgical Technique, Orthopedics Today, Mar. 1985.

Primary Examiner—Edgar S. Burr
Assistant Examiner—Moshe I. Cohen
Attorney, Agent, or Firm—Fisher, Christen & Sabol

[57] ABSTRACT

The invention relates to a device for supporting the rachis.

According to the invention, said device is characterized in that the pin is of constant corss-section throughout its length and presents a rough surface, and in that the anchoring members are provided with pressure means cooperating with said pin.

The invention finds an application in the straightening and/or support of a rachis, especially in preparation for an arthrodesis.

12 Claims, 12 Drawing Figures

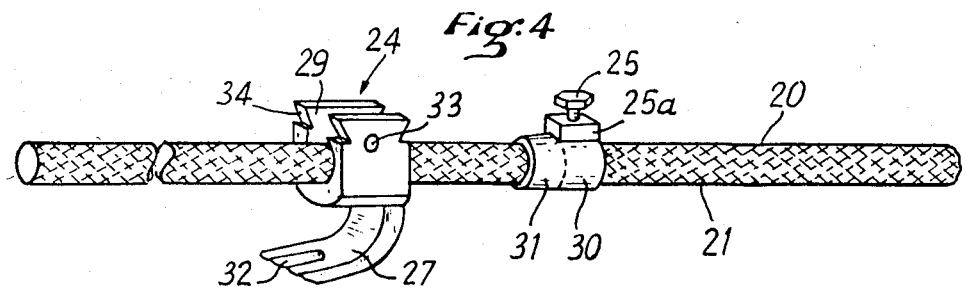
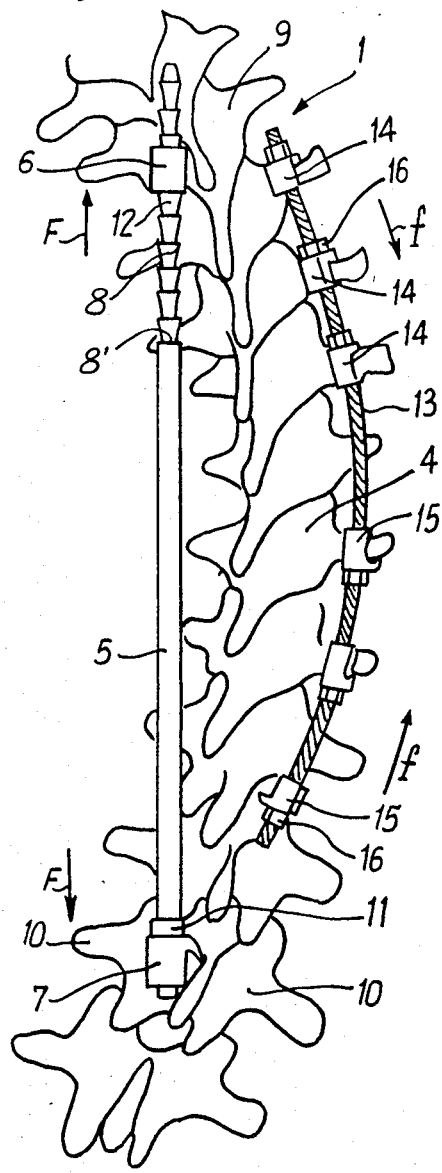
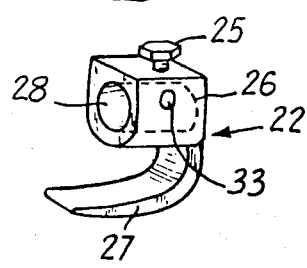
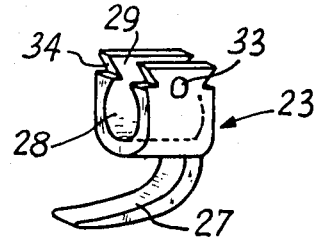
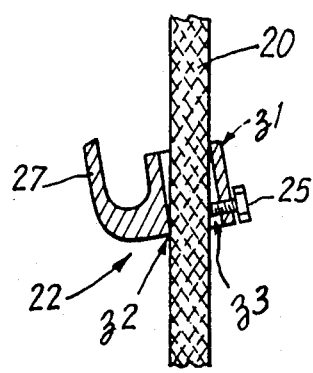

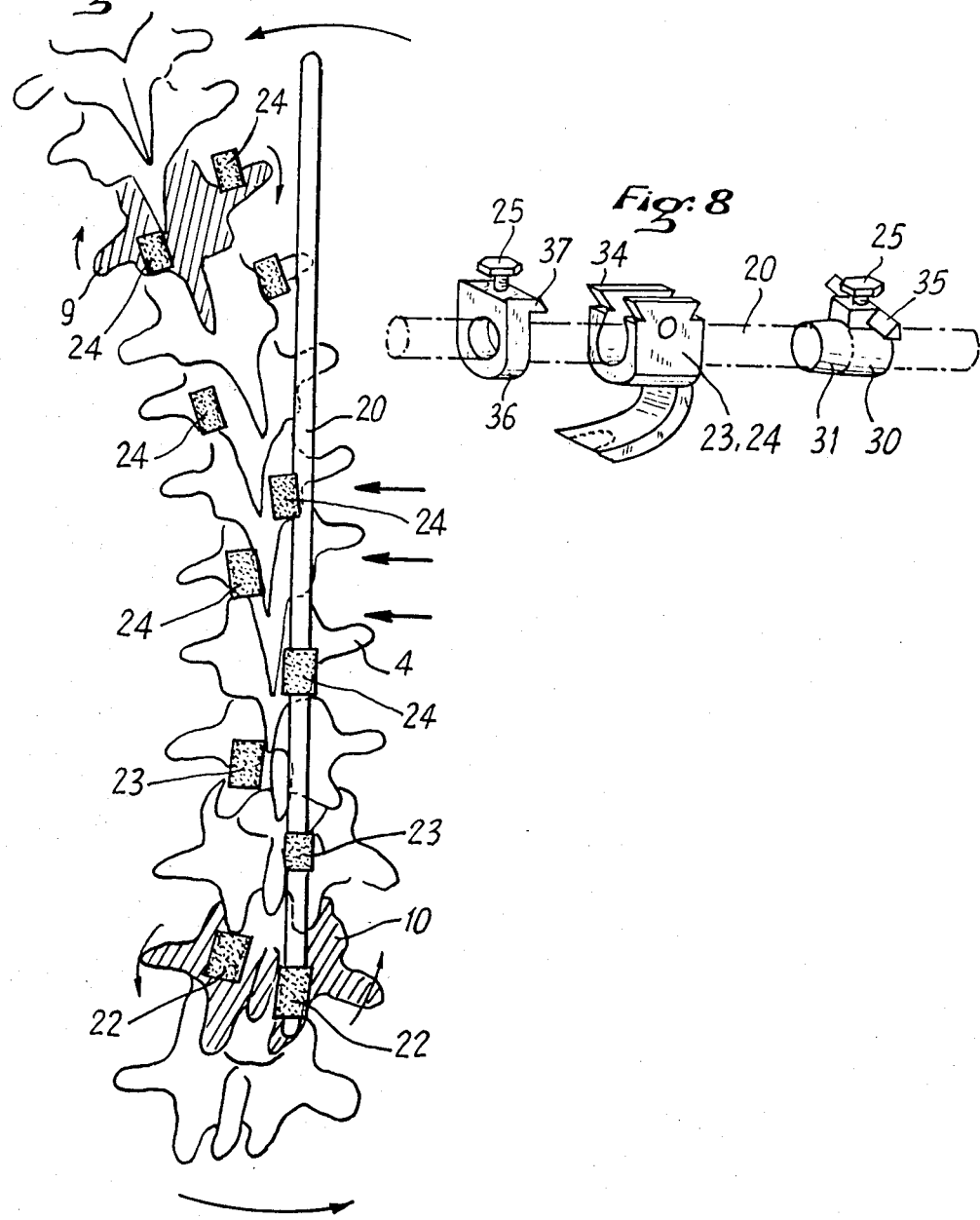
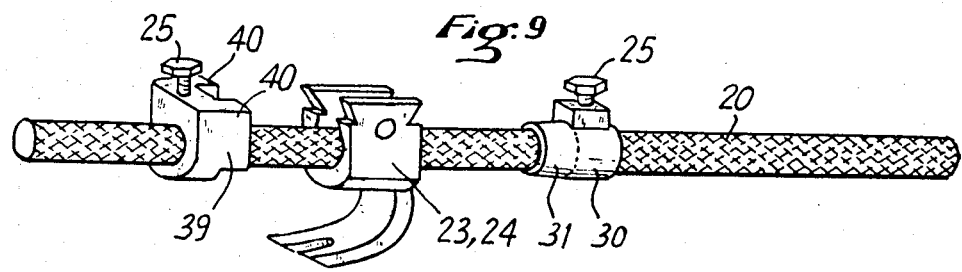

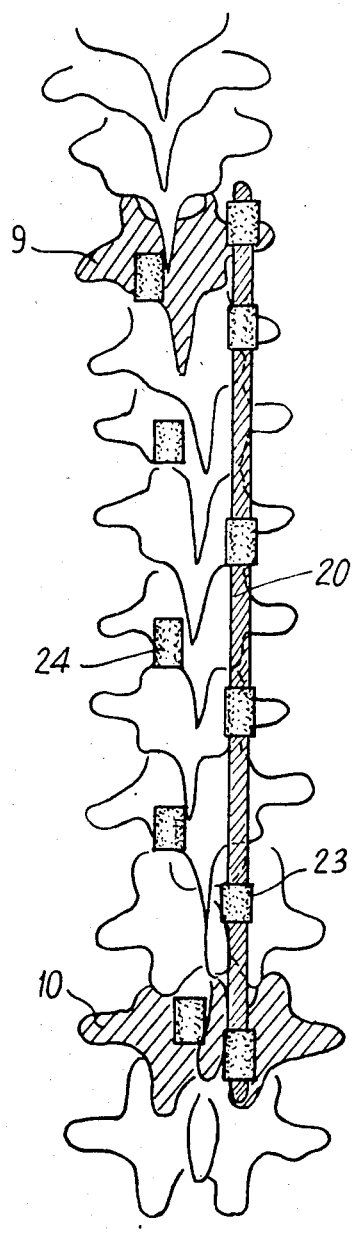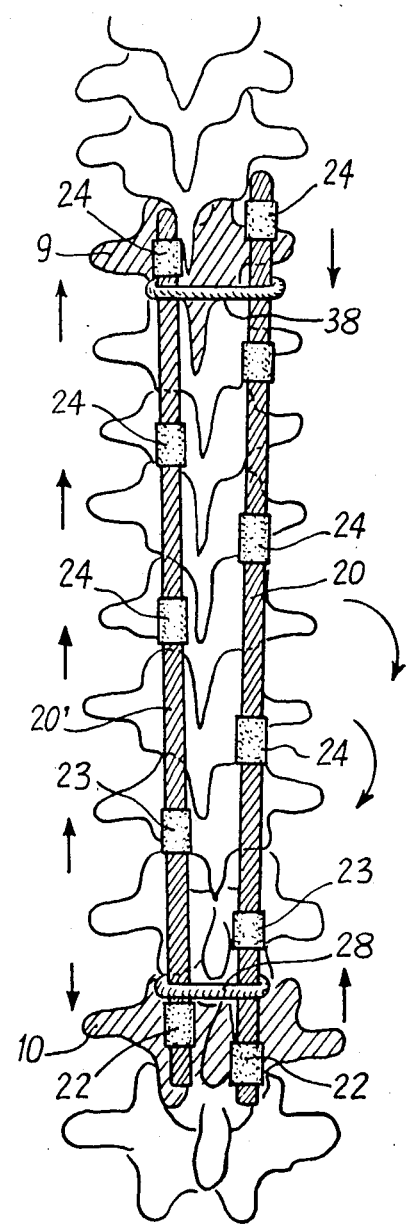

DEVICE FOR SUPPORTING THE RACHIS

The present invention relates to a device for supporting the rachis, fitted in by surgery. Said device may be used just for consolidating a rachis which needs to be consolidated (accidental fracture, for example) or else for correcting and supporting a rachis suffering from curvatures (scoliosis, cyphosis, for example). Although the device according to the invention is suitable for these two types of application, it is described hereinafter with reference to the surgical treatment of lateral curvatures of the spine.

Scoliosis, it is known, is a lateral curvature of the spine, together with rotation of certain vertebrae about their axis. Abnormal spinal flexure, resulting from said lateral curvature, is generally defined from specific points, namely the upper and lower extreme vertebrae between which said abnormal flexure is found, and the vertebra or vertebrae at the top thereof. Said upper and lower extreme vertebrae are those which have the least pivoted about their axis, but they are on the other hand, those most inclined on the median longitudinal axis, and their planes determine between them the angle of scoliotic curvature. The upper vertebra or vertebrae are those farthest from said median axis of the torso; they are slightly inclined or not inclined at all with respect to said axis, but, on the other hand, they are those which suffer the strongest rotation about their axis.

When the scoliotic curvature angle exceeds a certain threshold (around 50°), it becomes necessary to consider treating the scoliosis by surgery, said surgical treatment being called arthrodesis and consisting in welding together all the vertebrae of the scoliotic curvature, after a maximum correction thereof, by straightening and opening.

Such correction may be prepared before surgery by continuous traction of the rachis or by using corrective plasters. Said correction however, is completed and finalized during surgery. To this effect, a solid prop member is placed in the concavity of the rachidial curvature at least, said prop member consolidating the resulting correction and being able to strengthen the bone joint obtained by arthrodesis.

One instrumentation called the "HARRINGTON instrumentation" is already known to perform this. Said instrumentation consists of an elongation system, designed to be inserted in the concavity of the curvature, and of a compression system designed to be optionally inserted on the convex side. Often in fact, only the elongation system is used.

Said elongation system comprises two metallic anchoring members, of the hook type, resting against the extreme vertebrae of the curvature, and a metallic pin acting as a support, and permitting to keep the hooks one apart from the other, and as a result, to correct the scoliotic curvature. Said metallic pin, of circular cross-section, is provided at its lower part with a shoulder member, and at its upper part, with a notched portion, and it traverses the said hooks. The lower hook is fastened on the lamina of the lower extreme vertebra of the curvature and the metallic pin rests on said lower hook via the said shoulder member. The upper hook, which is fitted over the said pin, is placed under the zygapophysis of the upper extreme vertebra of the curvature and by external operations of traction (using for example retractors which rest against the notches of the upper part of the rod), the upper hook is drawn apart from the lower hook. Said upper hook goes past the notches of the notched portion of the pin, successively, and when the required correction is obtained, a locking device (such as a clip for example) is inserted between the upper hook and the notch nearest thereto.

The compression system is composed of transverse hooks traversed by a threaded pin provided with nuts. The upper hooks are fastened on the transverse processes of the the vertebrae of the curvature which are near the upper vertebra, whereas the lower hooks rest under the transverse processes or under the lamina of the vertebrae of the curvature which are close to the lower extreme vertebrae. A nut is associated to every hook and the required compression is obtained by actuating said nuts.

After fitting the instrumentation into place, an arthrodesis is carried out and the patient is made to wear a corset for support for a period varying between 6 and 12 months.

This type of instrumentation, although widely used, presents a number of disadvantages which are that:

(a) the opening of the curvature cannot be adjusted in continuous manner, but on the contrary in step-wise manner, each adjusting step being constituted by a notch of the notched portion of the elongation system. As a result, final adjustment of the opening of the rachis is achieved, not absolutely accurately, but to within a notch;

(b) opening of the curvature is achieved by applying very localized pressure at the level of the two extreme vertebrae of the curvature only, so that the pressure exerted on said vertebrae is very strong;

(c) the hooks, of the elongation system in particular can pivot about the metallic pin of said system, this enabling them to move with respect to their initial positioning;

(d) no direct re-centering action towards the axis of the torso is exerted by the instrumentation;

e) no real action of derotation is exerted on the top vertebrae;

(f) despite prolonged postsurgical support, breakage of the rod of the elongation system occurs, at the junction of the smooth parts with the notched parts, in 2.5% of cases.

It is the object of the present invention to overcome these disadvantages by developing a strong enough instrumentation to do away with the long postsurgical setting periods in a plaster or corset, during the vertebral synostosis.

This object is reached according to the invention with a device for strengthening the rachis, of the type comprising at least one pin and two anchoring members able to rest on vertebrae of said rachis and to be fixed in position on said pin, which device is remarkable in that said pin is of constant cross-section throughout its length and has a rough surface, and in that said anchoring members are provided with pressure means cooperating with said pin.

It is thus possible, due to the cooperation of the pressure means of said anchoring means with said pin, and to the surface condition of the latter, to adjust continuously and accurately the position of said anchoring members and, in doing so, adjust the opening of the scoliotic curvature. The invention further permits to interlock the anchoring members of the pin, so that no rotation is possible after actuating said pressure means. It also permits to multiply at will the anchoring members and to distribute them in such a way that each vertebra of the curvature is fixed in the required corrected position. And the pin having a constant cross-section, it has no longer any weak points, and breakage is prevented.

The pin may be milled or turned in order to have a roughness of surface. It will be noted that such roughness, in the case of arthrodesis, helps the fastening of the neoformed bone, so that the pin is firmly locked with the blended bone area.

The invention will be more readily understood on reading the following description with reference to the accompanying drawings, in which:

FIG. 1 diagrammatically illustrates the back of a patient suffering from scoliosis.

FIG. 3 shows a known instrumentation used for surgical correction of scoliosis.

FIGS. 4 to 9 illustrate the instrumentation according to the invention.

FIGS. 10, 11 and 12 illustrate a way of using the instrumentation according to the invention.

Figure 1:
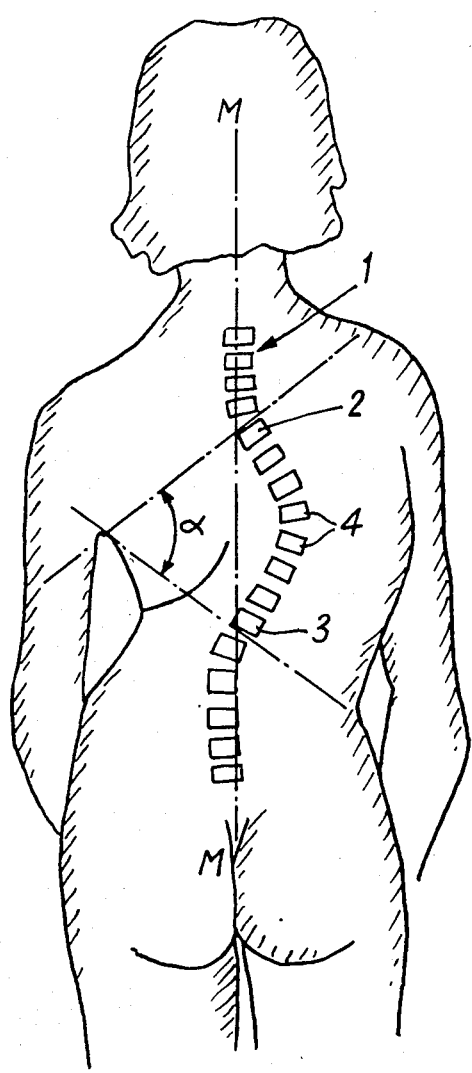

Referring first to FIG. 1, this diagrammatically shows the back of a patient suffering from scoliosis, assuming that the spine 1 is visible. The vertebrae are illustrated by small rectangular or trapezoidal shapes.

This patient has a scoliosis causing a spinal curvature towards the right. The scoliotic curvature can be defined owing to upper 2 and lower 3 extreme vertebrae of the curvature, and to vertebrae 4 situated at the top of said curvature. It will be noted that vertebrae 2 and 3 are those which are the most inclined on the median longitudinal axis MM of the body, whereas vertebrae 4 are those farthest from said axis. The angle $\alpha$ formed by the planes of vertebrae 2 and 3 is therefore a characteristic of the scoliotic curvature. As already indicated hereinabove, when angle $\alpha$ exceeds a certain threshold (about 50°), it becomes necessary to resort to arthrodesis and to fit in a support for the rachis.

Figure 2:
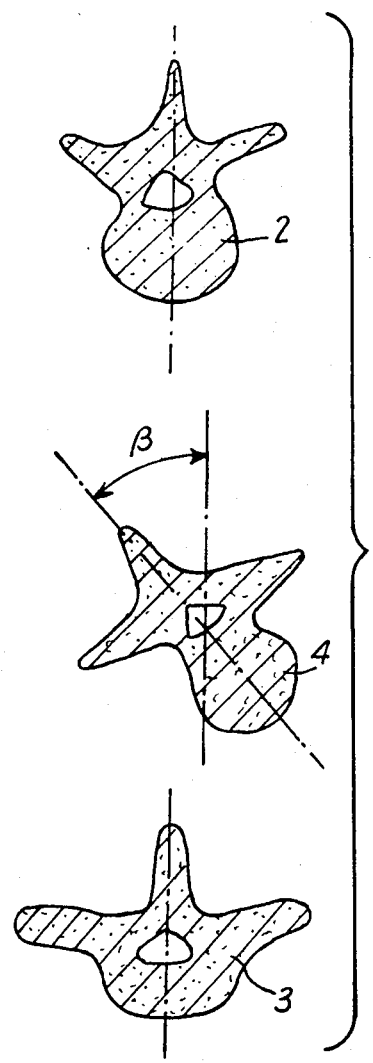
FIG. 2 illustrates the relative rotation of the vertebrae of a scoliotic rachis.

Also, and as illustrated in FIG. 2 showing diagrammatical views or each one of vertebrae 2, 3 and 4, the vertebra 4 at the top of the curvature is subjected to a rotation about its axis of amplitude $\beta$, due to scoliosis.

FIG. 3 illustrates the known method and instrumentation of HARRINGTON for correcting and strengthening a rachis, mentioned hereinabove. The elongation system comprises a cylindrical metal pin 5 able to cooperate at its two ends with anchoring devices 6 and 7. One of the ends 8 of the pin 5 is notched so as to enable to adjust the distance between the anchoring devices 6 and 7.

Normally, the upper anchoring member 6, namely that designed to be fixed next to the upper part of the rachis, is fastened to a thoracic vertebra 9 and its hook (not shown in FIG. 3) is facing upwardly and so shaped as to be insertable between the spinalis and a transverse process of said vertebra, between the upper and lower articular facets, said hook penetrating into the interarticular space and resting against the upper vertebra at that level.

In like manner, the lower anchoring member 7, namely that designed to be fixed on the side of the lower part of the rachis, is often resting on a lumbar vertebra 10. To this effect, its hook (not clearly shown in FIG. 3) is facing downwardly and rests on the vertebral lamina of said vertebra between the process and articular mass. The sliding movement of the lower anchoring member along pin 5 is limited upwards by a shoulder member 11 integral with said pin. Vertebrae 9 and 10 of FIG. 3 could be the extreme vertebrae 2 and 3 of FIG. 1.

After positioning the anchoring members 6 and 7 on their respective vertebra, said members are drawn apart as indicated hereinabove (arrows F), in order to reduce the scoliotic curvature. When the reduction is completed, the resulting spacing of the anchoring members is maintained by fitting in a locking clip 12 between a notch of part 8 and anchoring member 6.

FIG. 3 clearly shows the disadvantages a, b, c, and f, mentioned hereinabove as regards the elongation system and in particular the risk of the pin 5 breaking at the joining point 8' of the notched part 8 with the rest of the pin.

The instrumentation of HARRINGTON can further comprise a compression system composed of a flexible threaded pin 13, on which slide three upper anchoring members 14 and three lower anchoring members 15. Said anchoring members 14 and 15 each rest on a vertebra of the curvature of rachis 1 and are pressed against it by way of nuts 16 screwable on said threaded pin 13, so that they perform a compression action (arrow f).

It is thus obvious that, even with a compression system 13 to 16, the known instrumentation illustrated in FIG. 3 performs no direct re-centering action towards axis M—M and no derotation of vertebrae 4 at the top of the curvature (points d and e above).

In order to overcome disadvantages a, c and f inherent in the known instrumentation, the present invention has provided a support pin 20 to replace pin 5. As illustrated in FIG. 4, support pin 20 according to the invention is of constant cross-section throughout its length (therefore has no weak points) and its surface is provided with a multitude of asperities 21, obtained for example by milling or turning. Anchoring members 22, 23 or 24 (see FIGS. 4, 5 and 6) are also provided, which members can be fastened on pin 20, by means of pressure screws 25.

Anchoring member 22 (FIG. 5) comprises a body 26 to which is associated a hook 27. Said body 26 is provided with a through hole 28, whose diameter is sufficient to allow said member 22 to slide freely along pin 20, when said pin traverses hole 28. A screw 25 whose end issues into hole 28, is screwed into said body 26. Thus, as illustrated in FIG. 7, anchoring member 22 can be fixed in any position of pin 20, by screwing in screw 25, and after being threaded on said pin 20 by any end thereof.

The loading of member 22 causes same to pivot with respect to pin 20 (as exaggeratedly illustrated by way of example in FIG. 7) so that contact between pin 20 and and said member is made in three separate areas z1, z2 and z3, when screw 25 is tightened. The fastening of anchoring member 22 on pin 20 is then perfect, both in longitudinal position and in the pivoting movement of said pin, so that it can be used both in traction and in compression as well as in any rotation position.

FIGS. 4 and 6 show anchoring members 23 and 24 with open bodies. Indeed, since according to the invention, the anchoring members can be firmly fixed in any points of the pin 20, it is possible to multiply their numbers along said pin in order to increase the number of holds along the rachis; it is therefore advantageous to be able to position said anchoring members along said pin in a non-permanent manner, before fitting in the pin. To this effect, said anchoring members 23 and 24 comprise a groove 29 permitting to introduce the pin 20 and causing hole 28 to be open to the outside. Members 23 and 24 can thus be fitted at any moment on pin 20. To each member 23 or 24 is associated a locking element 30, equipped with a pressure screw 25 and being threaded over said pin before it is fitted. Each locking element 30 is in the form of a sleeve or bush with at least one conical part 31 adapted to cooperate with a correspondingly conical part of the hole 28 of members 23 or 24 (not shown in FIGS. 4 and 6) in order to lock said members on pin 20 by a wedge effect. Each element further comprises a body 25a which cooperates with a corresponding part of member 23, 24 with a view to blocking its rotation about pin 20.

Members 23 and 24 are identical, with the only exception that their hook 27 is slightly different. Hook 27 of member 23 which is designed to rest behind the lamina of the vertebra (such as that of member 22) is flat and solid, whereas hook 27 of member 24 designed to rest under the pedicle of the vertebra, is provided with a slot to this effect.

It will be noted that, for positioning purposes, the anchoring members are provided with holes 33 and/or with dovetail indentations 34 used as holds for gripping members such as pliers.

As illustrated in FIG. 8, said dovetail indentations 34 can also be used for joining up an element 23 or 24 with the pin 20, particularly when said element is required to withstand strong stresses. In this case, the locking element 30 is provided with wing members 35 adapted to engage into the facing indentations 34.

To further reinforce the joint of an element 23 or 24 with the pin 20, it is possible to provide an extra locking element 36, constituted by a ring equipped with a pressure screw 25 and a projection 37, adapted to engage the indentations 34 situated on the opposite side of locking element 30.

According to the variant embodiment shown in FIG. 9, a locking member is provided which comprises two side wings 40 adapted to grip the side walls of elements 23 and 24 and prevent, if necessary, said walls from moving apart. In addition, the front face of said anchoring members 23 and 24 comes to rest against a corresponding face of locking member 39, so that any pivoting movement of said members 23 and 24 is prevented, once screw 25 of member 39 is tightened.

FIGS. 10, 11 and 12 illustrate a possible way to apply the device according to the invention.

First, two anchoring members 22 are positioned at the level of the lower vertebra 10, one being inserted on the lamina on the concave side, and the other under the lamina on the convexe side. Then, moving upwards, either members 23 or members 24 are positioned every other vertebra, on the the concave side and on the convex side, and in such as way that said members on one side are offset with respect to the members of the other side (see FIG. 10). By bearing on the members 23 and 24 joined to the top vertebrae 4, it becomes possible to proceed to at least a partial derotation of said vertebrae.

Then a pin 20 is introduced into the lower member 22, on the convex side, and by using said pin as a lever, the latter is introduced successively in the members 23 and 24 which are above. This operation helps to reduce the curvature in the transverse direction, and the anchoring members of the concavity are aligned as best as they can be (see FIG. 11).

A second pin, identical to pin 20, and shown with the reference 20' in FIG. 12, is then introduced in the lower member 22 of the concavity, and having bent said pin 20' transversely if this proves necessary, the said pin is introduced successively in all the members 23 and 24 situated in the concavity of the curvature. In order to adapt to the anteroposterior physiological curvatures of the rachis, the pins may be bent within the sagittal plane without any danger of their breaking due to their structure.

Members 23 and 24 of pins 20 and 20' are of course held in position of said pins by way of the locking elements 30 mounted beforehand.

It will be noted that the fitting in of the two pins 20 and 20' tends to cause the derotation of the top vertebrae 4, with respect to the extreme vertebrae 9 and 10.

It is then proceeded, step-by-step, to the spreading upwardly from the middle of the curvature on the side of the concavity, of members 23 and 24 of the pin 20', and to bringing closer together members 22 and 24 of pin 20 on the side of the convexity, after which all said members are fixed in position by way of screws 25.

The two pins 20 and 20' are thereafter joined together by means of tractional cross-pieces 38, such as those described in French Pat. No. 73 33916 for example, after which an arthrodesis is conducted according to the conventional methods.

Obviously the fitting in method described with regard to FIGS. 10, 11, and 12 is only given by way of an illustration, as other ways may be used depending on every particular case.

What I claim is:

1. A device for strengthening the rachis comprising two pins which each extend over a plurality of vertebrae of said rachis, said pins being placed on opposite sides of said rachis, a plurality of hooked anchoring members mounted on each pin and positioned to rest on vertebrae of said rachis to support and derotate said vertabrae, and means to selectively fix said anchoring members in selected positions on said pins, said pins being of constant cross-section throughout their length and having roughened surfaces, each of said anchoring members being mounted for free, continuous motion along said pins except when fixed by said means to selectively fix, said means to selectively fix comprising a pressure screw perpendicular to said pins engageable with said roughened surface to fix said anchoring members in position on said pins, and said pins being joined together by tractional cross-pieces fitted between said pins.

2. A device as claimed in claim 1, wherein the surfaces of said pins are roughened by milling or turning.

3. A device as claimed in claim 1, wherein each of said pins can be bent to conform to the anteroposterior physiological curvatures of said rachis.

4. A device as claimed in claim 1, wherein said anchoring members comprise a body with a through hole for the free passage of said pin, said hole opening onto a groove which can be traversed by said pin, and are each associated with a locking element slidable on said pin, upon which it can be locked by means of a pressure screw, wherein said anchoring members can be interlocked with the associated locking elements by wedging.

5. A device as claimed in claim 4, wherein an additional locking element is associated with each anchoring member, which locking element is also slidable on the pin, upon which it can be locked by means of a pressure screw, each said additional locking element being placed on the side of the said anchoring members opposite the normal locking element.

6. A device as claimed in claim 4, wherein said locking element comprises in addition to its wedging means, other means which are engageable in complementary parts of said anchoring member.

7. A device as claimed in claim 1, wherein said pin is of circular cross-section.

8. A method of installing a device for strengthening a deformed rachis having a concave and convex side, in the transverse plane, said device comprising two pins of constant cross-section which have a surface roughened by milling or turning, a plurality of hooked anchoring members mounted on each pin and each having a pressure screw transverse to its associated pin, and at least two tractional cross-pieces, comprising the steps of:

(a) attaching said hooked anchoring members to vertebrae on both the concave and convex sides;

(b) inserting the first pin into the lowest of said anchoring members on said convex side of said rachis;

(c) manipulating said first pin so as to substantially straighten said rachis, derotate at least some of the vertebrae, and said first pin into the remaining anchoring members on said convex side of said rachis;

(d) inserting the second pin in said anchoring members on said concave side;

(e) completing the straightening of said rachis and the derotation of said vertebrae;

(f) fixing all said anchoring members in place on said pins by tightening said pressure screws to prevent sliding and rotational motion on said pins; and (g) joining said first and second pins together by means of at least two tractional cross-pieces.

9. A method as claimed in claim 8, wherein said anchoring members are attached to both the concave and convex sides of the lowest vertebra, and thereafter are attached to every other vertebra on the concave and convex sides, such that said members on one side are offset with respect to the members on the other side.

10. A method as claimed in claim 8, wherein said first pin installed on said convex side of said rachis is used as a lever to reduce the curvature of said rachis and align said anchoring members of said concave and said convex side.

11. A method as claimed in claim 8, wherein each of said pins are bent as required to conform to the anteroposterior physiological curvatures of said rachis.

12. A method claimed in claim 8, wherein said hooked anchoring members are further held in position by locking elements which are mounted on said pins before said pins are inserted in said anchoring members.

* * * * *

UNITED STATES PATENT AND TRADEMARK OFFICE
CERTIFICATE OF CORRECTION

PATENT NO. : 4,641,636

DATED : February 10, 1987

INVENTOR(S) : Yves P.C.A. Cotrel

It is certified that error appears in the above-identified patent and that said Letters Patent is hereby corrected as shown below:

[73] Assignee:  SOCIETE DE FABRICATION DE MATERIEL ORTHOPEDIQUE SOFAMOR
Berck-Plage, France Signed and Sealed this Second Day of February, 1988

Attest:

DONALD J. QUIGG

Attesting Officer

Commissioner of Patents and Trademarks